US006447766B1

(12) United States Patent
Pelus et al.

(10) Patent No.: US 6,447,766 B1
(45) Date of Patent: *Sep. 10, 2002

(54) METHOD OF MOBILIZING HEMATOPOIETIC STEM CELLS

(75) Inventors: Louis Martin Pelus, Richboro; Andrew Garrison King, Blue Bell; Yanqiu Qian, King of Prussia, all of PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/467,155

(22) Filed: Dec. 20, 1999

Related U.S. Application Data

(63) Continuation of application No. 08/999,804, filed on Nov. 26, 1997, now abandoned, which is a continuation-in-part of application No. PCT/US96/17074, filed on Oct. 24, 1996, which is a continuation-in-part of application No. 08/547,262, filed on Oct. 24, 1995, now abandoned, which is a continuation-in-part of application No. PCT/US94/06264, filed on Jun. 3, 1994, now Pat. No. 6,080,398, which is a continuation of application No. 07/073,800, filed on Jun. 8, 1993, now abandoned.

(51) Int. Cl.[7] .................. A61K 38/19; C12N 15/19; C07K 14/52

(52) U.S. Cl. .................. 424/85.1; 530/300; 530/350; 530/351; 536/23.5; 435/69.1; 435/69.5; 514/2; 514/4

(58) Field of Search .................. 424/85.1; 530/350; 530/351, 300, 324; 536/23.5; 435/69.5; 514/1

(56) References Cited

U.S. PATENT DOCUMENTS 6,080,398 A * 6/2000 Pelus et al. .................. 424/85.1

FOREIGN PATENT DOCUMENTS

| WO | WO 91/07988 | 6/1991 |
|---|---|---|
| WO | WO 92/00327 | 1/1992 |
| WO | WO 92/01039 | 1/1992 |
| WO | WO 92/06196 | 4/1992 |
| WO | WO 94/28916 | 12/1994 |
| WO | WO 96/19234 | 6/1996 |

OTHER PUBLICATIONS

Geiger T and Clarke S. J Biol Chem 262(2), Jan. 15, 1987, pp785–794. Deamidation, Isomerization, and Racemization at Asparaginyl and Aspartyl residues in peptides.*
E. Brandt, et al., "A Novel Molecular Variant of the Neutrophil–Activating Peptide NAP–2 With Enhanced Biological Activity is Truncated at the C–Terminus: Identification By Antibodies With Defined Epitope Specificity", (1993), Molecular Immunology, vol. 30:11, pp. 979–991.

B. Moser, et al., "Interleukin–8 Antagonists Generated by N–terminal Modification", (1993), Journal of Biological Chemistry, vol. 268:10, pp. 7125–7128.
C.A. Hérbert, et al., "Endothelial and Leukocyte Forms of IL–8", (1990), Journal of Immunology, vol. 145:9, pp. 3033–3040.
J. Van Damme, "The neutrophil–activating proteins interleukin 8 and β–thromboglobulin: in vitro and in vivo comparison of $NH_2$–terminally processed forms", (1990), European Journal of Immunology, vol. 20, pp. 2113–2118.
A.M. Gronenborn, et al., "Modeling, the three–dimensional structure of the monocyte chemo–attractant and activating protein MCAF/MCP–1 on the basis of the solution structure of interleukin–8", (1991), Protein Engineering, vol. 4:3, pp. 263–269.
J.J. Oppenheim, et al., "Properties of the Novel Proinflammatory Supergene "Intercrine" Cytokine Family", Annual Review of Immunology, vol. 9, pp. 617–648.
S. Nourshargh, et al., "A Comparative Study of the Neutrophil Stimulatory Activity In Vitro and Pro–Inflammatory Properties In Vivo of 72 Amino Acid and 77 Amino Acid IL–8", (1992), Journal of Immunology, vol. 148:1, pp. 106–111.
I. Clark–Lewis, et al., "Structure–Activity Relationships of Interleukin–8 Determined Using Chemically Synthesized Analogs", (1991), Journal of Biological Chemistry, vol. 266:34, pp. 23128–23134.
Cao, et al., "gro–β, a –C–X–C– Chemokine, Is an Angiogenesis Inhibitor That Suppresses the Growth of Lewis Lung Carcinoma in Mice", (1995), J. Exp. Med., vol. 182, pp. 2069–2077.
M.Y. Stoeckle, "Post–transcriptional regulation of groα, β, γ, and IL–8 mRNAs by IL–1 β", (1991), Nucleic Acids Research, vol. 19, No. 4, pp. 917–920.
Laterveer, et al., "Rapid Mobilization of Hematopoietic Progenitor Cells in Rhesus Monkeys by a Single Intravenous Injection of Interleukin–8", (1996), Blood, vol. 87, No. 2, pp. 781–788.
Proost, et al., "Identification of Novel Granulocyte Chemotactic Protein (GCP–2) from Human Tumor Cells", (1993), Journal of Immunology, vol. 150:3, pp. 1000–1010.
Cuenca, et al., "Characterization of GRO α, β, and γ expression in human colonic tumours: potential significance of cytokine involvement", (1992), Surical Oncology, vol. 1, pp. 323–329.
Becker, et al., "Constitutive and stimulated MCP–1, Groα, β, and γ, expression in human airway epithelium and bronchoalveolar macrophages", (1994), American Journal of Physiology, vol. 266, pp. L278–288.

(List continued on next page.)

*Primary Examiner*—Prema Mertz
*Assistant Examiner*—Sarada C Prasad
(74) *Attorney, Agent, or Firm*—Linda E. Hall; William T. King; Stephen A. Venetianer

(57) ABSTRACT

A method of mobilizing hematopoietic stem cells from the bone marrow to the peripheral circulation is provided by administering to an animal an effective amount of mature, modified or multimeric forms of KC, groβ, groα, or groγ.

2 Claims, 3 Drawing Sheets

OTHER PUBLICATIONS

L.B. To, et al., "Single High Doses of Cyclophosphamide Enable the Collection of High Numbers of Hemopoietic Stem Cells from the Peripheral Blood", (1990), Int'l. Society for Experimental Hematology, vol. 18, pp. 442–447.

Laterveer, et al., "Interleukin–8 Induces Rapid Mobilization of Hematopoietic Stem Cells With Radioprotective Capacity and Long–Term Myelolymphoid Repopulating Ability", (1995), Blood, vol. 85, pp. 2269–2275.

* cited by examiner

METHOD OF MOBILIZING HEMATOPOIETIC STEM CELLS

This is a continuation of application Ser. No. 08/999,804, now abandoned, filed Nov. 26, 1997; which is a continuation-in-part of International Application No. PCT/US96/17074, filed on Oct. 24, 1996, which is a continuation-in-part of Ser. No. 08/547,262, filed on Oct. 24, 1995 now abandoned which is continuation-in-part of International Application No. PCT/US94/06264, now U.S. Pat. No. 6,080,398, filed on Jun. 3, 1994, which is continuation of Ser. No. 07/073,800, filed on Jun. 8, 1993 now abandoned.

FIELD OF THE INVENTION

The present invention relates generally to methods for mobilizing hematopoietic stem cells and to a novel deamidated chemokine.

BACKGROUND OF THE INVENTION

All the members of the intercrine or chemokine family are basic heparin-binding polypeptides which have four cysteine residues which form two disulfide bridges. All these proteins which have been functionally characterized appear to be involved in proinflammatory and/or restorative functions.

In clinical situations for the use of high dose chemotherapy, the biomolecule of choice has been G-CSF. Generally, in such treatment, patients are primed with a low dose of a chemotherapeutic agent like cyclophosphamide. During the remission, the patient is treated with a CSF, such as G-CSF, which causes eventual mobilization of cells from the bone marrow to the peripheral circulation for harvesting of leukophoresed blood. The patient is thereafter administered a high dose of chemotherapy to induce clinical remission of their cancer. The resultant bone marrow failure is treated by infusion of the stored blood cells collected previously. This procedure may be modified, e.g., by the omission of the initial dose of chemotherapy and/or alternate blood collection protocols.

While the use of these hematopoietic stem cell transplantation techniques looks promising, multiple apheresis procedures are required to harvest sufficient stem cells for successful engraftment to treat severe myelosuppression when G-CSF is used alone [see, e.g., Bensinger et al, *Blood*, 81:3158 (1993) and R. Haas et al, *Sem. in Oncology*, 21:19 (1994)]. Thus, despite these significant advances and the availability of certain regulatory biomolecules, delayed recovery of hematopoiesis remains an important source of morbidity and mortality for myelosuppressed patients.

There exists a continuing need in the art for compositions and methods to enhance hematopoietic recovery, particularly in cases of chemotherapy associated myelosuppression.

SUMMARY OF THE INVENTION

In one aspect, the present invention provides for the use of a chemokine in the preparation of a medicament for the stimulation of hematopoietic stem cells. This chemokine includes proteins derived from KC, groβ, groα, and groγ, including mature, modified, and multimeric forms of these chemokines.

In yet a further aspect, the present invention provides a method for mobilizing hematopoietic stem cells in an animal comprising administering to an animal an effective amount of a mature or modified or multimeric chemokine as described herein.

In a further aspect, the present invention provides a novel deamidated form of a modified groβ (amino acids 5–73 of SEQ ID NO: 3) which is useful for mobilizing hematopoietic stem cells.

Other aspects and advantages of the present invention are described further in the following detailed description of the preferred embodiments thereof.

DETAILED DESCRIPTION OF THE INVENTION

Figure 1:
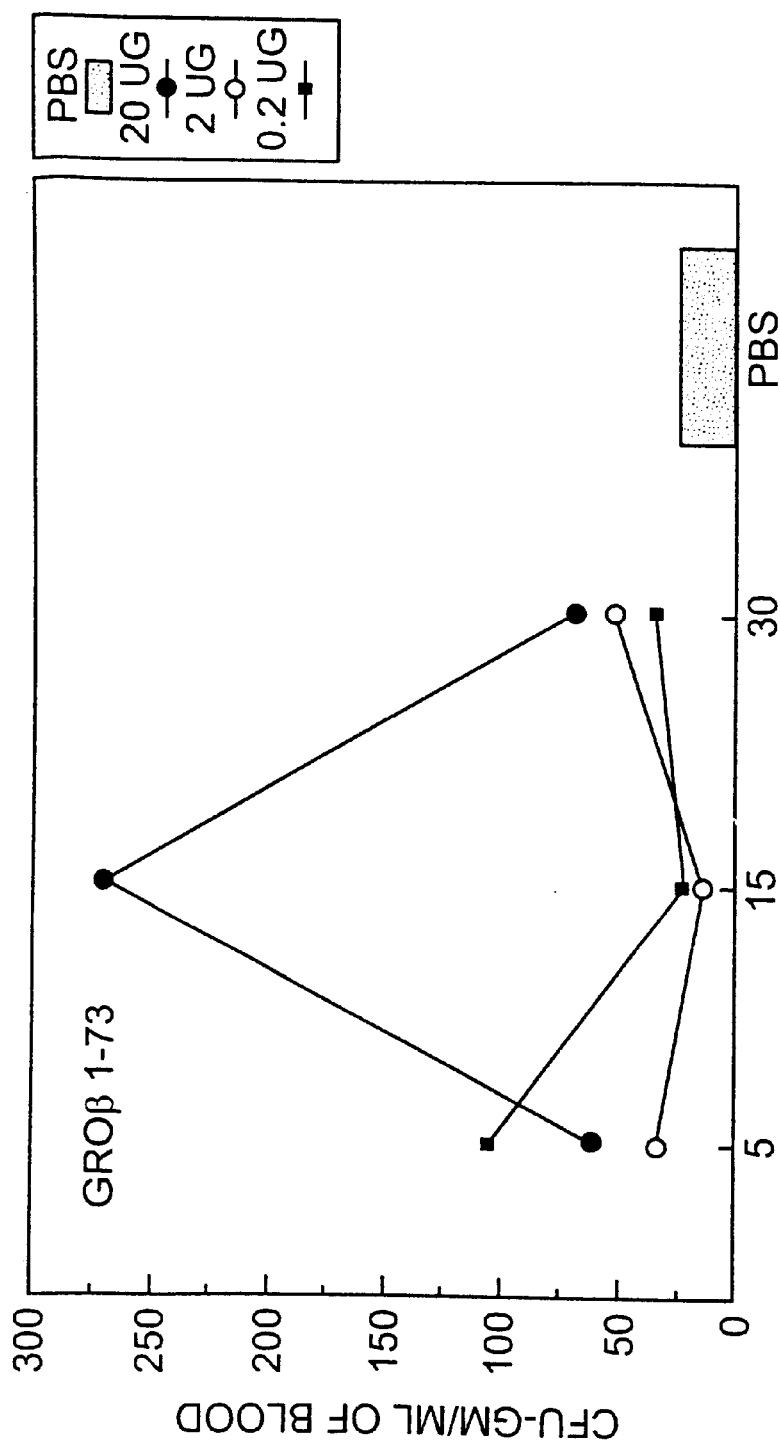
FIG. 1 is a graph demonstrating the effect of groβ (amino acids 1–73 of SEQ ID NO: 3) in the single agent mobilization assay of Example 1.
Figure 2:
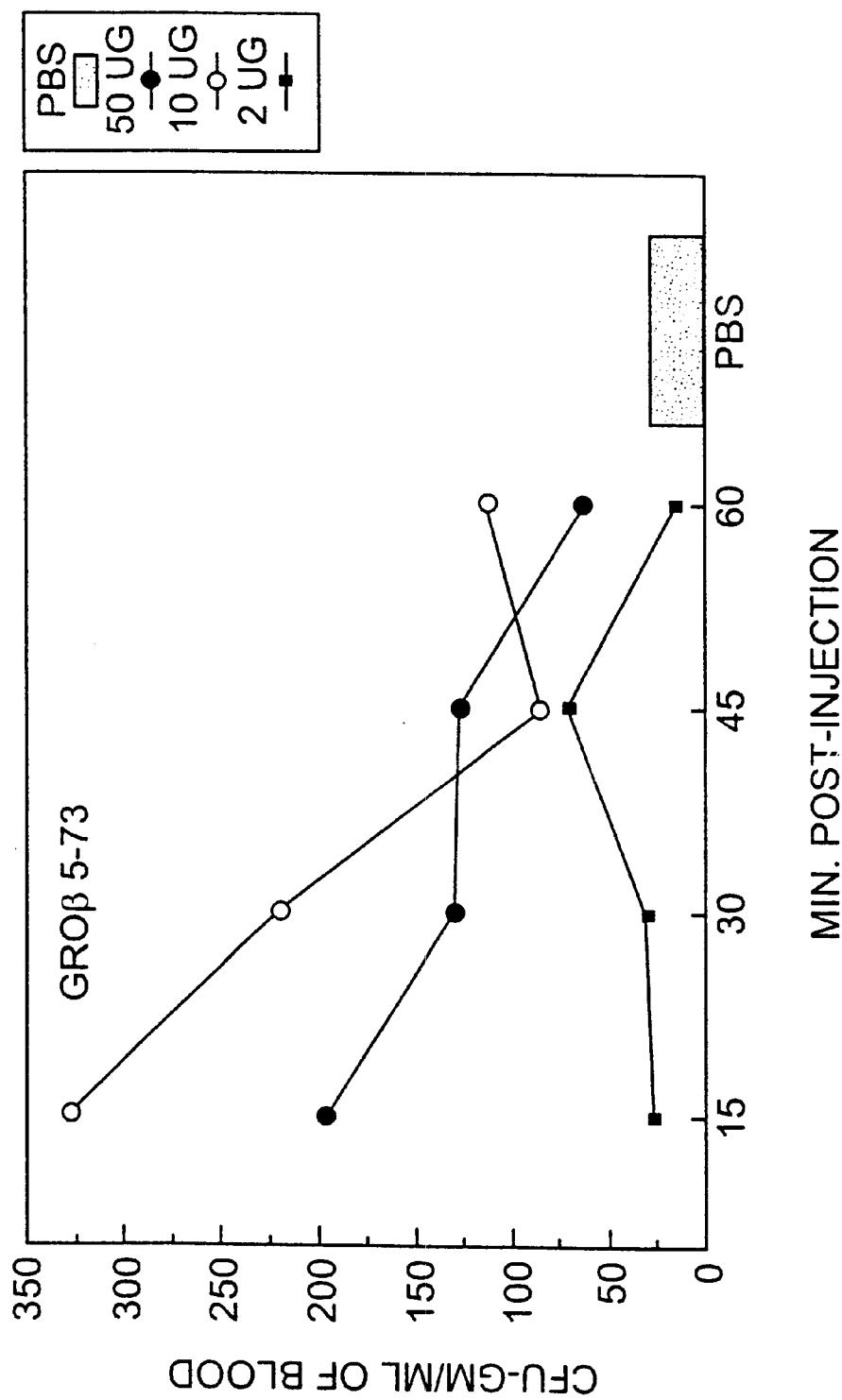
FIG. 2 is a graph demonstrating the effect of modified groβ (amino acids 5–73 of SEQ ID NO: 3) in the single agent mobilization assay of Example 1.
Figure 3:
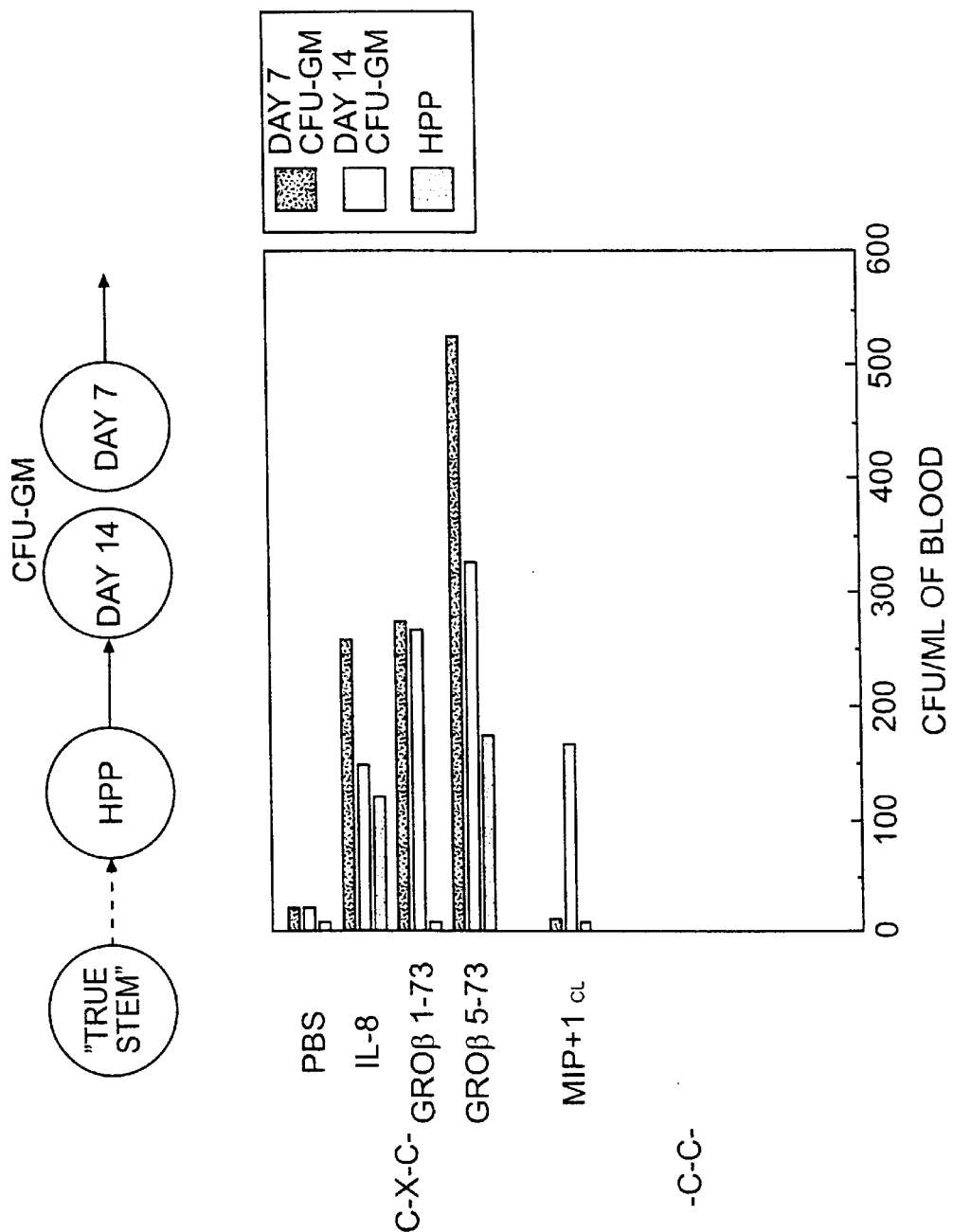
FIG. 3 is a bar graph demonstrating the comparison of phosphate buffered saline (PBS), IL-8, groβ (amino acids 1–73; SEQ ID NO: 3) and modified groβ (amino acids 5–73 of SEQ ID NO: 3) in the single agent mobilization assay.

The present invention provides methods for the treatment of myelosuppression, by mobilizing hematopoietic stem cells from the bone marrow into the peripheral blood using the mature or modified or multimeric chemokines described herein.

The present invention also provides a novel deamidated form of a truncated groβ (amino acids 5–73 of SEQ ID NO. 3) a pharmaceutical composition thereof, and its use in the treatment of myelosuppression.

The deamidation occurs primarily in position 69 (using the 1–73 nomenclature to define the full length groβ). The deamidation forms the α or β isomeric aspartate products; aspartic acid and iso-aspartic acid.

This deamidated form has surprisingly been shown to retain the mobilizing activity of the parent truncated groβ (5–73). This was unexpected as other peptides, have lost activity when the Asn has been changed to an Asp or Iso-Asp (Bongers et al. Int J Pept Protein Res. 1992 April; 39(4): 364–74; Friedmen et al, Int J Pept Protein Res. 1991 January: 37(1) 14–20). The deamidated (position 69) truncated groβ (amino acids 5–73 of SEQ ID NO. 3) alone and in a mixture with the non-deamidated truncated groβ parent also may be used for the treatment of myelosuppression by mobilizing hematopoietic stem cells from the bone marrow into the peripheral blood.

I. Definitions

As defined herein, "hematopoietic synergistic factor" or "HSF" refers to a class of proteins, including the naturally occurring chemokines and modified chemokines, which are characterized by having synergistic activity in stimulating hematopoiesis when administered in vivo and in vitro with another hematopoietic factor, such as a colony stimulating factor, or combined with naturally circulating CSFs.

The term "mature chemokines" also known as "intercrines", as used herein defines the proteins conventionally referred to in the art as KC, groα, groβ, and groγ. For convenience, the amino acid sequences of the murine protein KC which contains 72 residues is provided in SEQ ID NO: 1. These sequences are available from Genbank, accession number J04596. The sequences of the human protein groα (aa 1–73) are provided in SEQ ID NO:2. The sequences of the human protein groβ (amino acids 1–73) are provided in SEQ ID NO: 3. The sequences of the human protein groγ are provided in SEQ ID NO: 4. The cDNA and amino acid sequences of groγ are also provided in International Patent Application, Publication No. WO 92/00326 (Jan. 9, 1992). These groγ sequences have further been published in International Patent Application, Publication No. WO 94/29341 (Dec. 22, 1994), which is incorporated by reference herein.

The term "modified chemokines" is defined as in the above-referenced International Application. The modified chemokines are derived from KC, groβ, groα, and groγ, more preferably from groβ, groα, and groγ, and most preferably from groβ. The modified chemokines include desamino proteins characterized by the elimination of between about 2 to about 8 amino acids at the amino terminus of the mature protein. These desamino chemokines useful in the method of the invention are preferably characterized by removal of about 2 to about 8 amino acids from the amino terminus of the mature protein. Most preferably, the modified chemokines are characterized by removal of the first 4 amino acids at the amino-(N-) terminus. Optionally, particularly when expressed recombinantly, the desamino chemokines useful in this invention may contain an inserted N-terminal Met. The N-terminal methionine which is inserted into the protein for expression purposes, may be cleaved, either during the processing of the protein by a host cell or synthetically, using known techniques. Alternatively, if so desired, this amino acid may be cleaved through enzyme digestion or other known means.

Also included by the term modified chemokine are analogs or derivatives of these proteins which share the biological activity of the mature protein. As defined herein, such analogs and derivatives include modified proteins also characterized by alterations made in the known amino sequence of the proteins, e.g., the proteins provided in SEQ ID NOS: 1–4. Such analogs are characterized by having an amino acid sequence differing from that of the mature protein by 8 or fewer amino acid residues, and preferably by about 5 or fewer residues. It may be preferred that any differences in the amino acid sequences of the proteins involve only conservative amino acid substitutions. Conservative amino acid substitutions occur when an amino acid has substantially the same charge as the amino acid for which it is substituted and the substitution has no significant effect on the local conformation of the protein or its biological activity. Alternatively, changes such as the introduction of a certain amino acid in the sequence which may alter the stability of the protein, or permit it to be expressed in a desired host cell may be preferred. Another characteristic of these modified proteins may be enhanced biological activity in comparison to the mature protein.

By the term "multimeric protein" or "multimer" is meant herein multimeric forms of the mature and/or modified proteins useful in this invention, e.g., dimers, trimers, tetramers and other aggregated forms. Such multimeric forms can be prepared by synthesis or recombinant expression and can contain chemokines produced by a combination of synthetic and recombinant techniques as detailed below. Multimers may form naturally upon expression or may be constructed into such multiple forms. Multimeric chemokines may include multimers of the same modified chemokine. Another multimer may be formed by the aggregation of different modified proteins. Still another multimer is formed by the aggregation of a modified chemokine of this invention and a known, mature chemokine. Preferably, a dimer or multimer useful in the invention would contain at least one desamino chemokine protein and at least one other chemokine or other protein characterized by having the same type of biological activity. This other protein may be an additional desamino chemokine, or another known protein.

II. Proteins Useful in the Invention

In general, the chemokines useful in the method of the invention include the mature chemokines, or the modified and multimeric proteins derived therefrom, which are described in detail in International Patent Application, Publication No. WO 94/29341. Desirably, these chemokines are selected from KC, groα, groβ and groγ, and most preferably the chemokine is groβ.

In one preferred embodiment, the method of the invention utilizes a desamino chemokine protein of the invention. This protein comprises the amino acid sequence of mature chemokine useful in the invention truncated at its N terminus between amino acid positions 2 and 8 of SEQ ID NOS: 1–4. Preferably, the desamino protein of the invention has a protein sequence spanning amino acids 5 to 73 of SEQ ID NOS: 2–4, or amino acids 5 to 72 of SEQ ID NO: 1. Most preferably, the method of the invention is desamino groβ, which has the protein sequence spanning amino acids 5 to 73 of SEQ ID NO: 3 or the deamidated desamino groβ which has the protein sequence spanning amino acids 5 to 73 of SEQ ID NO. 3 wherein the amino acid in position 69 has been deamidated to the Iso aspartic acid or aspartic acid or a mixture of deamidated and nondeamidated desamino groβ spanning amino acids 5 to 73 of SEQ ID NO: 3.

As described in WO 94/29341, similar modifications can be made to the KC, groα and groγ proteins which are useful in the methods of the invention. These proteins are all described in the literature and are known to those of skill in the art.

Preferred multimeric proteins useful in this invention include, dimers or multimers containing at least one desamino chemokine protein and at least one other chemokine or other protein characterized by having the same type of biological activity. This other protein may be an additional desamino chemokine, or another, known protein. For example, a desirable dimer useful in the methods of the invention comprises two desamino proteins as described above, preferably linked by disulfide bonds. A desirable multimer may be an aggregate of two or more desamino groβ proteins, particularly two proteins consisting of amino acids 5–73 of SEQ ID NO: 3. Alternatively, another dimer of the invention may be a desamino groβ protein of the invention in combination with a mature groβ protein. Similarly, various combinations of dimers or other multimeric forms may contain a combination of the mature or modified groβ and other chemokines, such as the KC, groα and groγ proteins. For example, a desamino groβ protein of the invention may form a dimer with an unmodified mature groα protein. One of skill in the art may obtain other desirable multimers using the modified chemokines of the invention. However, the use of multimeric forms of two or more different modified proteins as defined herein are useful in the method of this invention. The chemokine employed in this method may also be a multimeric form of a modified chemokine as discussed above and another known mature protein.

These proteins and monomers have been described in detail in the literature and may be synthesized, or produced recombinantly, using conventional techniques and/or the techniques described in International Patent, Publication No. WO 94/29341.

III. Pharmaceutical Compositions

Desirably, the chemokines useful in the method of the invention are used in the preparation of medicaments and/or are useful in the form of a pharmaceutical composition.

Thus, the chemokines can be formulated into pharmaceutical compositions and administered in the same manner as described in, e.g., International Patent Applications, Publication No. WO 90/02762 (Mar. 22, 1990) and Publication No. WO 94/29341 (Dec. 22, 1994).

These medicaments or pharmaceutical compositions useful in the mobilization of hematopoietic stem cells contain a therapeutically effective amount of a mature, modified or multimeric chemokine as defined herein and an acceptable pharmaceutical carrier. As used herein, the term "pharmaceutical" includes veterinary applications of the invention.

The term "therapeutically effective amount" refers to that amount of a chemokine, whether in monomeric or multimeric form, which is useful for mobilizing stem cells in sufficient amounts to achieve the desired physiological effect.

Generally, a mature, modified or desamino chemokine useful in the invention (e.g., groβ) is administered in an amount between about 0.01 ng/kg body weight to about 100 mg/kg body weight and preferably about 0.01 ng/kg body weight to 10 mg/kg body weight per dose. Desirably, when a multimeric chemokine is used in the method of the invention, the medicament or composition contains amounts of the multimeric protein at the lower end of this range. Preferably, these pharmaceutical compositions are administered to human or other mammalian subjects by injection. However, administration may be by any appropriate internal route, and may be repeated as needed, e.g. one to three times daily for between 1 day to about one week.

Suitable pharmaceutical carriers are well known to those of skill in the art and may be readily selected. Currently, the preferred carrier is saline. Optionally, the pharmaceutical assays of the invention may contain other active ingredients or be administered in conjunction with other therapeutics. Suitable optional ingredients or other therapeutics include those conventional for treating conditions of this nature, e.g. other anti-inflammatories, diuretics, and immune suppressants, among others. Desirably, these modified chemokines are particularly well suited for administration in conjunction with colony stimulating factor.

IV. Methods for Mobilizing Hematopoietic Stem Cells

The invention provides improved methods of treating conditions characterized by immunosuppression or low numbers of hematopoietic stem cells and cells differentiated therefrom, including, without limitation, inflammation, fever, viral, fungal, and bacterial infections, cancer, myelopoietic dysfunction, hematopoiesis disorders, aplastic anemia, and autoimmune diseases, and conditions characterized by low production and/or differentiation of hematopoietic and/or bone marrow cells. This method involves administering to a selected mammal a pharmaceutical composition of the invention. Preferably, this composition is administered together with, or contains, a colony stimulating factor. Suitable sources of colony stimulating factor are well known and include, e.g., natural, synthetic and recombinant GM-CSF, M-CSF, G-CSF and IL-3. In another preferred embodiment, a desamino chemokine useful in the invention can be administered in vivo, and permitted to act in synergy with the natural colony stimulating factors found in a selected patient.

In one preferred embodiment, the method of the invention uses the desamino chemokines described herein in conjunction with GM-CSF (or G-CSF). The use of a modified chemokine, such as a desamino groβ or mixture of deamidated desamino groβ and desamino groβ, according to the method of the invention in combination with G-CSF (this combination has been observed to have synergy) permits lower doses of G-CSF to be administered to a patient, reducing the extremely unpleasant side effects caused by GM-CSF (G-CSF).

The mature chemokines and the modified or multimeric chemokines useful in the method of the invention are characterized by the ability to mobilize hematopoietic stem cells when administered alone, or by having synergistic activity in stimulating hematopoiesis when administered in vivo and in vitro with another hematopoietic factor, such as a colony stimulating factor or a growth factor, or combined with naturally circulating CSFs, or administered in a protocol with chemotherapy.

In one embodiment, the invention provides a method for mobilizing hematopoietic stem cells in an animal by administering to an animal an effective amount of the composition or medicament containing a mature chemokine selected from human groβ [SEQ ID NO: 3], human groα [SEQ ID NO: 2], human groγ [SEQ ID NO: 4], and murine KC [SEQ ID NO: 1].

In another, embodiment of this invention, a method for mobilizing hematopoietic stem cells in an animal involves administering to an animal an effective amount of a modified protein derived from a chemokine selected from groβ, groα, groγ, and KC. As a preferred embodiment there is provided a method for mobilizing hematopoietic stem cells in an animal by administering to an animal an effective amount of a modified protein derived from chemokine human groβ [SEQ ID NO: 3].

In still another aspect, the present invention provides a method for mobilizing hematopoietic stem cells in an animal comprising administering to an animal an effective amount of a multimeric protein, which comprises an association of at least one chemokine as described above and a second chemokine.

In the practice of the method of mobilizing hematopoietic stem cells, the term "effective amount" of these proteins may be defined as that amount which, when administered to a patient by suitable means, mobilizes hematopoietic stem cells and increases the number of hematopoietic stem cells in the peripheral blood. This amount is expected to be higher than the amount required to stimulate the growth or development of hematopoietic progenitor cells. The effective amount increases in the circulation the cells which are differentiated from the hematopoietic stem cells in applicable clinical or veterinary situations. A desirable effective amount may be about 0.01 nglkg to 10 mg/kg body weight per dose.

Suitable means of administration for mobilizing stem cells include, without limitation, bolus injection or incremental administration of the effective amount by injection, i.v. drip, or any other appropriate internal route including subcutaneous injection. Dosages may be repeated as needed, e.g. one to three times daily for between 1 day to about one week.

Additionally, the method of this invention employing the mature chemokines, or modified or multimeric chemokines identified above may be used in peripheral blood hematopoietic stem cell transplantation regimens. For example, following an optional initial dose of a chemotherapeutic agent, the mature chemokines or modified or multimeric chemokines identified above are administered in place of the CSFs now used to mobilize hematopoietic stem cells from the bone marrow to the peripheral circulation for harvesting, as well as for readministration following high doses of chemotherapy. Suitable chemotherapy agents include, without limitation, the well-known agents such as cyclophosphamide, cisplatinum, ARA-C, 5-fluorouracil, etopside, epirubicin, carboplatin, busulfan, mitoxantrone and carmustine. When administered with the chemokines according to this invention, the amounts of the chemotherapeutics are those amounts conventionally employed, i.e., about 1.2 g/m$^2$ etopside, 800 mg/m$^2$ ARA-C, 200 mg/kg cyclophosphamide, etc. See for such dosages Hass et al, *Seminars in Oncol.*, 21:19–24 (1994), incorporated herein by reference.

The chemokines identified above may be used to complement the conventionally used CSFs in treatment regimens. Alternatively, the chemokines identified above may be used in combination therapies with other hematopoietic regulatory biomolecules, such as the molecules involved in hematopoiesis above-referenced, or with growth factors, conventional pharmaceuticals and/or drugs, for the same purposes. Suitable sources of such growth factors are well known and include, without limitation, natural, synthetic and recombinant GM-CSF, G-CSF, stem cell factor, and Flt-3 ligand. Other suitable biomolecules include (S)-5-oxo-L-prolyl-a-glutamyl-L-a-aspartyl-N$^8$-(5-amino-1-carboxypentyl)-8-oxo-N$^7$-[N-{N-(5-oxo-L-prolyl)-L-a-glutamuyl}-L-a-aspartyl]-L-threo-2,7,8-triaminooctanoyl-lysine [(pGlu-Glu-Asp)$_2$-Sub-(Lys)$_2$] [Pelus et al, *Exp. Hematol.*, 22:239–247 (1994)].

Still other pharmaceuticals and drugs for co-administration may be readily selected by on e of skill in the art.

The advantages of the use of this invention in replacement or in conjunction with traditional methods of peripheral blood hematopoietic stem cell transplantation are that more rapid recovery of PMNs and/or platelets occur than with bone marrow transplantation, the risk of infection is reduced and the method permits potentially higher curative doses of chemotherapy, or a series of dose intensified chemotherapy to be administered.

The following examples are illustrative only and do not limit the scope of the invention.

EXAMPLE 1

Mobilization Assay

Chemokines derived from KC [SEQ ID NO: 1, groβ [SEQ ID NO: 3] and groγ [SEQ ID NO:4] including modified and multimeric chemokines are prepared using known techniques. See, e.g., WO 94/29341 for additional discussion relating to the preparation of such chemokines. These chemokines are tested for the ability to mobilize hematopoietic stem cells in mice. Each chemokine is assayed in concentrations of 50, 10 and 2 micrograms/mouse and administered via subcutaneous, intramuscular, intraperitoneal, intravenous, or oral route. The kinetics of chemokine mobilization of hematopoietic stem cells are monitored in 15 minute intervals over a period of 60 minutes by collecting blood samples by cardiac puncture from the mice. The mobilized hematopoietic stem cells are fractionated and collected by separation over a Lympholyte-MÔ density gradient. Cells are washed for future use.

Mature blood cell elements are enumerated using a TechniconÔ H1 hematology analyzer, equipped with veterinary software. Mobilization of mature inflammatory cells, such as polymorphonuclear (PMN) cells, eosinophils, and basophils are taken in to account when evaluating the overall potential inflammatory profile.

To monitor early and later hematopoietic progenitor cells, a CFU-GM assay is performed, i.e. blood samples collected during the mobilization phase are assessed for colony forming units (CFU-GM) at days 7 and 14. Cells are adjusted to 10$^6$ cells/ml in McCoys medium without serum. A single layer agar system consisting of McCoys medium enriched with nutrients (NaHCO$_3$, pyruvate, amino acids, vitamins and HEPES buffer), 0.3% Bacto agar, and 15% fetal bovine serum is used. Cells from the blood samples (final concentration of 10$^5$ cells/ml) are added to the agar system. The agar plates are incubated at 37° C., 7.5% CO$_2$ for 7–14 days. Colonies of proliferating cells (CFU-GM) are counted utilizing a microscope.

In addition, early hematopoietic high proliferative potential (HPP) progenitors, are counted in the day 14 CFU cultures.

The chemokine IL-8, which mobilizes hematopoietic stem cells as a single factor, is included in these studies as a positive control.

Preliminary experiments have shown that administration of groβ [SEQ ID NO: 3] results in a dose dependent mobilization of CFU-GM, similar to the results with the control. Modified groβ, the N-terminal 4 amino acid truncation protein (aa5–73) of groβ mobilized significantly greater numbers of hematopoietic progenitor cells than groβ (amino acids 1–73) or IL-8. No significant changes (>3 fold) in mature cell elements were observed in groβ treated mice, indicating specific mobilization of hematopoietic progenitor cells. This result demonstrates that the modified desamino chemokines may have enhanced mobilization characteristics compared to the mature proteins.

EXAMPLE 2

Mobilization Assay in Combination with Hematostimulants

Hematostimulants are assayed in combination with the chemokines identified above as mobilization factors. The hematostimulants include G-CSF, GM-CSF, (S)-5-oxo-L-prolyl-a-glutamyl-L-a-aspartyl-N$^8$-(5-amino-1-carboxypentyl)-8-oxo-N$^7$-[N-{N-(5-oxo-L-prolyl)-L-a-glutamuyl}-L-a-aspartyl]-L-threo-2,7,8-triaminooctanoyl-lysine [(pGlu-Glu-Asp)$_2$-Sub-(Lys)$_2$] [Pelus, cited above] and FLT-3 ligand. Any G-CSF mimetic, i.e., a hematostimulant which is not a CSF like G-CSF or GM-CSF, but has hematopoietic activity, may be used.

In combination assays, the hematostimulant, e.g., G-CSF, is administered at 50 microgramsg/kg to mice four days prior to the chemokines or modified or multimeric chemokines derived from KC [SEQ ID NO: 1], groβ [SEQ ID NO: 3] and groγ [SEQ ID NO:4]. As in Example 1, the dose of chemokine and time of blood collection is varied.

A CFU-GM assay is performed as described above in Example 1, with SCF, IL-1 and GM-CSF as the source of colony stimulating activity. Mature blood cell elements, early and later progenitors are measured as for Example 1.

Combination studies with hematostimulant pre-treatment utilizes MIP-1α as the positive control.

EXAMPLE 3

Murine Peripheral Blood Stem Cell Transplantation Model

A. Mobilization of Primitive Long Term Repopulating Stem Cells

The following experiment was performed in an in vivo stem cell transplantation model to determine if N-terminally truncated groβ [aa 5–73 of SEQ ID NO: 3; termed groβ3-T] mobilizes primitive long term repopulating stem cells. In this model, gamma irradiated mice are recipients of bone marrow cells. Mice are followed for 100 days for survival.

The ability of blood stem cells collected from mice treated with either PBS, groβ-T (50 micrograms at 15–30 min.), G-CSF (1 micrgram/mouse BID×4), or G-CSF, then groβ-T to rescue otherwise lethally irradiated mice. Blood mononuclear cells (up to 1E+6) collected from PBS treated mice protein 0–10% of the mice 100 days post transplant. Mice receiving marrow cells as the assay positive control were at 100% survival as of day 100. Mobilized blood cells (1E+6 cells/mouse) collected from mice treated with groβ-T alone protected 70% of recipients. Mobilized blood cells (1E+6 cells/mouse) collected from G-CSF treated donors protected 80% of recipients. Mobilized blood cells collected from donors treated with G-CSF and groβ-T mobilize greater numbers of repopulating cells than G-CSF alone.

B. Mobilization of Peripheral Blood Stem Cells

The rate at which peripheral blood stem cells mobilized by groβ-T recovered mature blood cell lineages in an irradiated host was evaluated. 1E+6 low density peripheral blood cells (LDPBC) were injected into irradiated recipients and bled by cardiac puncture on days 7–19 post irradiation. LDPBC from the different groups were collected under optimal conditions for CFU-GM mobilization. The groups compared in this experiment were PBS, groβ-T alone (50 micrgram, 15 min), G-CSF (BID×5 days, 1 microgram/mouse alone), and groβ-T+G-CSF. Normal mice were bled daily for comparison to the transplanted animals.

Mice which received a transplant from PBS treated donors failed to recover mature blood cell elements and died. The rate of neutrophil recovery in the mice which received cells mobilized by truncated groβ was faster than those who received G-CSF mobilized cells. Mice transplanted with LDPBC mobilized by the combination of groβ-T+G-CSF resulted in a faster neutrophil recovery rate than groβ-T mobilized cells.

The recovery of platelet counts in these same mice followed the same pattern: groβ-T+G-CSF>groβ-T>G-CSF>>PBS. However, on day 19, platelet counts are still far from returning to normal values. These data indicate that groβ-T mobilized blood stem cells engraft in recipient mice, with resultant neutrophil and platelet recovery rates equal to or better than G-CSF mobilized stem cells.

EXAMPLE 4

Preparation of Groβ-T

Expression of GROβ-T

GROβ-T was expressed intracellularly in *E. coli* using LW14 host strain and an expression vector (pEAHy). Expression was controlled by the phase lamda PL promotor on the vector and a temperature sensitive cI857 repressor. Expression is induced by temperature shift of the growing cells. The induced protein was in the cell lysate insoluble pellet. Cells harvested from 10 liter fermentation was frozen −70° C. Cell lysis, Refolding, and Purification of GROβ-T Frozen cells were dispersed in 20 mM sodium citrate buffer pH 6.0 containing 40 mM NaCl and 2 mM EDTA (10 ml/g of cells) and lysed by two passages through a Microfluidics M110Y or Gaulin at 11,000 psi. The lysate was centrifuged at 10,000 g for one hour at 4° C. All of GROβ-T was in the pellet and lysate supernatant was discarded. The pellet was solubilized in 2M Guanidine HCl, 50 mM Tris HCl pH 7.0 (2 ml/g of cells) for two hours at 25° C. The solution was diluted in an equal volume of water and insoluble material was removed by centrifugation at 15,000 g for one hour. In order to convert all GROβ-T to the reduced form, the supernatant was adjusted to 20 mM DTT and was incubated for two hours at 25° C. The solution was diluted to 10 ml/g of cells with 5 mM HCl, which resulted in mass precipitation. The precipitate (contained no GROβ-T) was removed by centrifugation at 25,000 g for one hour. The clear supernatant was dialyzed (3K)or diafiltered (Filtron 3 K cut off) against 5 mM HCl. The reduced GROβ-T in 5 mM HCl was neutralized to pH 7.5 with 2 M Trizma base and was adjusted to 1 mM cysteamine, 0.2 mM cystamine, and 1 mM EDTA. Reoxidation was allowed for 2 hours at 25° C. The solution was adjusted to pH 6.5 with 1 M HCl and applied to Toyopearl SP 650 M column (2 ml resin/g of cells) equilibrated with 50 mM Mes pH 6.5 (Buffer A). The column was washed with 5-column volume of Buffer A and then with 5-column volume of 22 % of Buffer B (1 M NaCl in Buffer A). GROβ-T was eluted with 35% of Buffer B at>95% purity. The pool was flown-through Q-Sepharose in 0.4 M NaCl in order to remove any associated DNA or endotoxin, was dialyzed in 1 mM potassium phosphate pH 6.5 (Buffer P) containing 50 mM NaCl and was applied to hydroxyapatite column (BioRad Macro-Prep Ceramic Hydroxyapatite Type I). HA column was washed with 0.15 M NaCl in Buffer P to remove impurities and GROβ-T was eluted with 0.5 M NaCl in Buffer P. HA pool was dialyzed against saline and stored at −70° C., where it was stable indefinitely. To obtain homogeneous nondeamidated GROβ-T, the pool from SP column was fractionated using C18 RP-HPLC column instead of Q-Sepharose and HA columns. The SP-pool was adjusted to 0.1% TFA and applied to Vydac C18 (2.2×25 cm, 10 micron, Nest Group) which was equilibrated with 12.5% Buffer R (80% acetonitrile in 0.1% TFA). The column was washed with one column volume of 30% Buffer R. GROβ-T was eluted with 5-column volume of a linear gradient, 30 to 40% of Buffer R. The pool from C18 column was lyophilized to dryness, resuspended in saline at 10 mg/ml, dialyzed extensively against saline, and stored at −80° C. before using it in animal studies.

Preparation of Deamidated GROβ-T

When above purified GROβ-T was incubated in 0.1 M Na Phosphate buffer pH 8.0 for five days at 25° C., GROβ-T was completely deamidated based on the analysis by capillary electrophoresis. Only a single site of deamidation was identified by NMR spectra as N69D.

EXAMPLE 5

Detection of Deamidation Products of Groβ-T using Reversed Phase HPLC

Resolution of iso-Asp 69, Asp 69 and the native Asn 69 forms of Groβ-T in their disulfide bridged state (non-reduced) was achieved using a Zorbax 300SB-C8 reversed phase HPLC column (2.1 mm×150 mm, part number 883750.906, Rockland Technologies, Inc.) fitted to a HP1090 chromatography system (Hewlett Packard). A typical analysis involved injection of 16 μg of Groβ-T mixture dissolved in 40 μl 0.1% TFA in water. Separation was achieved using linear gradient elution (Table 1) by mixing Buffer A containing (1 ml of 'Baker Analyzed' HPLC grade TFA added to 1 l of Nanopure II water) and Buffer B containing 80% acetonitrile, 0.1% TFA (800 ml of HPLC grade acetonitrile added to 200 ml of water followed by 1 ml of HPLC grade TFA). Column temperature was maintained at 60° C. and peaks were detected at both 210 and 215 nm.

TABLE 1

| Time (min) | Flow (ml/min) | Buffer A (%) | Buffer B (%) |
| --- | --- | --- | --- |
| 0.0 | 0.2 | 71.0 | 29.0 |
| 60.0 | 0.2 | 68.0 | 32.0 |
| 65.0 | 0.2 | 68.0 | 32.0 |

TABLE 1-continued

| Time (min) | Flow (ml/min) | Buffer A (%) | Buffer B (%) |
|---|---|---|---|
| 68.0 | 0.2 | 71.0 | 29.0 |
| 80.0 | 0.2 | 71.0 | 29.0 |

Iso-Asp 69, Asp 69 and native Asn 69 Groβ-T peptides gave retention times of 44.2 min, 51.9 min and 47.7 min respectively.

Using a slightly modified gradient and the same chromatography condition as described above, analysis of both native and Groβ-T deamidated products with reduced disulfide bridges (reduced) was achieved.

TABLE 2

| Time (min) | Flow (ml/min) | Buffer A (%) | Buffer B (%) |
|---|---|---|---|
| 0.0 | 0.2 | 68.0 | 32.0 |
| 60.0 | 0.2 | 64.0 | 36.0 |
| 65.0 | 0.2 | 64.0 | 36.0 |
| 68.0 | 0.2 | 68.0 | 32.0 |
| 80.0 | 0.2 | 68.0 | 32.0 |

Reduced Iso-Asp 69, Asp 69 and native Asn 69 Groβ-T peptides gave retention times of 43.7 min, 50.6 min and 46.9 min respectively.

Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. A modified chemokine consisting of amino acids 5 to 73 of SEQ ID NO: 3 wherein the amino acid number 69 has been deamidated to aspartic acid or isoaspartic acid.

2. A multimeric chemokine comprising an aggregation of two or more desamino gro-β proteins of claim 1.

* * * * *

SEQUENCE LISTING

```
<160> NUMBER OF SEQ ID NOS:  4

<210> SEQ ID NO 1
<211> LENGTH: 72
<212> TYPE: PRT
<213> ORGANISM: Mus musculus

<400> SEQUENCE: 1

Ala Pro Ile Ala Asn Glu Leu Arg Cys Gln Cys Leu Gln Thr Met Ala
1               5                   10                  15

Gly Ile His Leu Lys Asn Ile Gln Ser Leu Lys Val Leu Pro Ser Gly
            20                  25                  30

Pro His Cys Thr Gln Thr Glu Val Ile Ala Thr Leu Lys Asn Gly Arg
        35                  40                  45

Glu Ala Cys Leu Asp Pro Glu Ala Pro Leu Val Gln Lys Ile Val Gln
    50                  55                  60

Lys Met Leu Lys Gly Val Pro Lys
65                  70

<210> SEQ ID NO 2
<211> LENGTH: 73
<212> TYPE: PRT
<213> ORGANISM: Homo sapiens

<400> SEQUENCE: 2

Ala Ser Val Ala Thr Glu Leu Arg Cys Gln Cys Leu Gln Thr Leu Gln
1               5                   10                  15

Gly Ile His Pro Lys Asn Ile Gln Ser Val Asn Val Lys Ser Pro Gly
            20                  25                  30

Pro His Cys Ala Gln Thr Glu Val Ile Ala Thr Leu Lys Asn Gly Arg
        35                  40                  45

Lys Ala Cys Leu Asn Pro Ala Ser Pro Ile Val Lys Lys Ile Ile Glu
    50                  55                  60

Lys Met Leu Asn Ser Asp Lys Ser Asn
65                  70

<210> SEQ ID NO 3
<211> LENGTH: 73
<212> TYPE: PRT
<213> ORGANISM: Homo sapiens
```

```
<400> SEQUENCE: 3

Ala Pro Leu Ala Thr Glu Leu Arg Cys Gln Cys Leu Gln Thr Leu Gln
 1               5                  10                  15

Gly Ile His Leu Lys Asn Ile Gln Ser Val Lys Val Lys Ser Pro Gly
            20                  25                  30

Pro His Cys Ala Gln Thr Glu Val Ile Ala Thr Leu Lys Asn Gly Gln
            35                  40                  45

Lys Ala Cys Leu Asn Pro Ala Ser Pro Met Val Lys Lys Ile Ile Glu
        50                  55                  60

Lys Met Leu Lys Asn Gly Lys Ser Asn
65                  70

<210> SEQ ID NO 4
<211> LENGTH: 73
<212> TYPE: PRT
<213> ORGANISM: Homo sapiens

<400> SEQUENCE: 4

Ala Ser Val Val Thr Glu Leu Arg Cys Gln Cys Leu Gln Thr Leu Gln
 1               5                  10                  15

Gly Ile His Leu Lys Asn Ile Gln Ser Val Asn Val Arg Ser Pro Gly
            20                  25                  30

Pro His Cys Ala Gln Thr Glu Val Ile Ala Thr Leu Lys Asn Gly Lys
            35                  40                  45

Lys Ala Cys Leu Asn Pro Ala Ser Pro Met Val Gln Lys Ile Ile Glu
        50                  55                  60

Lys Ile Leu Asn Lys Gly Ser Thr Asn
65                  70
```